United States Patent [19]

Omura

[11] Patent Number: 4,609,645

[45] Date of Patent: Sep. 2, 1986

[54] MACROLIDE ANTIBIOTICS, PHARMACEUTICAL COMPOSITIONS AND METHODS OF USE

[76] Inventor: Satoshi Ōmura, 12-7 Seta 5-Chome, Setagaya-Ku, Tokyo, Japan

[21] Appl. No.: 593,461

[22] Filed: Mar. 26, 1984

[30] Foreign Application Priority Data

Mar. 30, 1983 [JP] Japan .................................. 58-54677

[51] Int. Cl.$^4$ ....................... A61K 31/71; C07H 17/08
[52] U.S. Cl. ......................................... 514/30; 536/7.1
[58] Field of Search ............................ 536/7.1; 514/30

[56] References Cited

U.S. PATENT DOCUMENTS

| 4,321,362 | 3/1982 | Baltz et al. | 536/7.1 |
| 4,362,881 | 12/1982 | Hamill et al. | 536/7.1 |
| 4,366,247 | 12/1982 | Baltz et al. | 536/7.1 |
| 4,477,443 | 10/1984 | Umezawa et al. | 424/180 |

FOREIGN PATENT DOCUMENTS 0052361  5/1982  European Pat. Off. ............. 536/7.1

OTHER PUBLICATIONS

Omura et al., "Biochemical and Biophysical Research Communications", vol. 107, No. 2, 1982, pp. 554–560.
Omura et al., "Jour. of the Amer. Chem. Soc.", 91:12, 1969, pp. 3401–3404.
Daggett et al., Amer. Type Culture Collection, "Catalogue of Strains 1", 15th Ed., 1982, p. 205, Rockville, MD 20852-1776.
Omura et al., "Jour. of Antibiotics", vol. XXXVI, No. 7, 1983, pp. 927–930.
Sadakane et al., "Jour. of Antibiotics", vol. XXXVI, 1983, pp. 921–922.
Omura et al., "Jour. of Antibiotics", vol. XXXIII, No. 12, 1980, pp. 1570–1572.
Omura et al., "Chem. Pharm. Bull.", vol. 28, No. 6, 1980, pp. 1963–1965.
Baltz et al., "Antimicrob. Agents Chemother.", vol. 20, No. 2, 1981, pp. 214–225.
Matsubara et al., "Chem. Pharm. Bull.", vol. 30, No. 1, 1982, pp. 97–110.
Omura et al., "The Microbial Transformation of Tylosin by the Spiramycin-Producing Strain, *Streptomyces ambofaciens* KA-1028," *J. Antibiotics* 33 (8), 911–912 (1980).
Sadakane et al., "Hybrid Biosynthesis of Derivatives of Protylonolide and M-4365 by Macrolide-Producing Microorganisms," *J. Antibiotics* 35 (6), 680–687 (1982).
Chemical Abstracts, vol. 101:111343n (1984).

*Primary Examiner*—Johnnie R. Brown
*Attorney, Agent, or Firm*—Nancy J. Harrison; Arthur R. Whale

[57] ABSTRACT

Macrolides PTL-448 A and B, which can be prepared by aerobic cultivation of *Streptomyces ambofaciens* ATCC 15154 in the presence of a macrolide intermediate selected from protylonlide, 5-O-mycaminosylprotylonolide, 20-hydroxy-5-O-mycaminosylprotylonolide and 20-oxo-5-O-mycaminosylprotylonodide, and macrolides PTL-448 C and D, which can be prepared by acidic hydrolysis of PTL-448 A and B are useful antibiotics.

16 Claims, 8 Drawing Figures

MACROLIDE ANTIBIOTICS, PHARMACEUTICAL COMPOSITIONS AND METHODS OF USE

BRIEF SUMMARY OF THE INVENTION

This invention relates to the new macrolide antibiotics PTL-448 A, B, C and D. PTL-448 A and B are produced by aerobically cultivating Streptomyces ambofaciens ATCC 15154 or ATCC 23877 in the presence of a macrolide intermediate selected from protylonolide, 5-0-mycaminosyl-protylonolide, 20-hydroxy-5-0-mycaminosylprotylonolide and 20-oxo-5-0-mycaminosylprotylonolide. PTL-448 C and D are produced by hydrolytic cleavage of mycarose from PTL-448 A and B, respectively. The PTL-448 A, B, C and D compounds and their pharmaceutically acceptable salts are useful antibiotics.

DESCRIPTION OF THE DRAWINGS

In the accompanying drawings

DETAILED DESCRIPTION

This invention relates to novel macrolides, their synthesis, formulations and use as antimicrobial agents.

There exist in the literature numerous references to macrolide derivatives similar to the well-known antibiotic tylosin. For instance, U.S. Patent Specifications Nos. 4,362,881 and 4,366,247 describe the preparation of protylonolide (also known as tylactone):

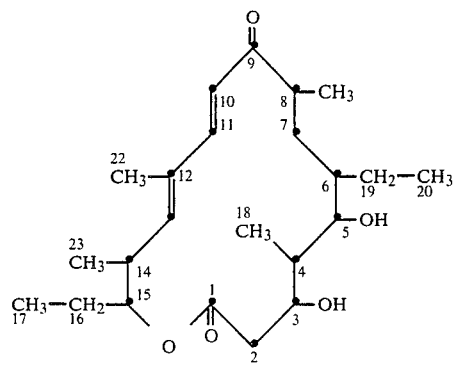

Derivatives thereof, for example, 5-0-mycaminosyl-protylonolide, 20-hydroxy-5-0-mycaminosylprotylonolide and 20-oxo-5-0-mycaminosylprotylonolide are described in Chem. Pharm. Bull., 29, 1963 (1980), Antimicrob. Agents Chemother., 20, 214 (1981), Chem. Pharm. Bull. 30, 97 (1982) and Biochem. Biophys. Res. Commun., 107, 554 (1982).

In accordance with the invention, it has now been discovered that the macrolide antibiotics, hereinafter referred to as PTL-448 derivatives, produced via the aerobic cultivation of Streptomyces ambofaciens ATCC 15154 in a culture medium containing assimilable sources of carbon, nitrogen and inorganic salts, and in the presence of one or more macrolide intermediates selected from protylonolide, 5-0-mycaminosyl-protylonolide, 20-hydroxy-5-0-mycaminosylprotylonolide and 20-oxo-5-O-mycaminosylprotylonolide, possess useful antibacterial properties.

There are two direct products of the fermentation: PTL-448 A and B. Two further products, PTL-448C and D, can be produced by hydrolytic cleavage of the mycarose sugar from A and B, respectively. These demycarosyl products are particularly active.

The PTL-448 derivatives of the invention are stable white powders and have physico-chemical properties as shown in Tables 1 and 2.

TABLE 1

Physico-chemical properties of antibiotics A, B, C and D

Figure 1:
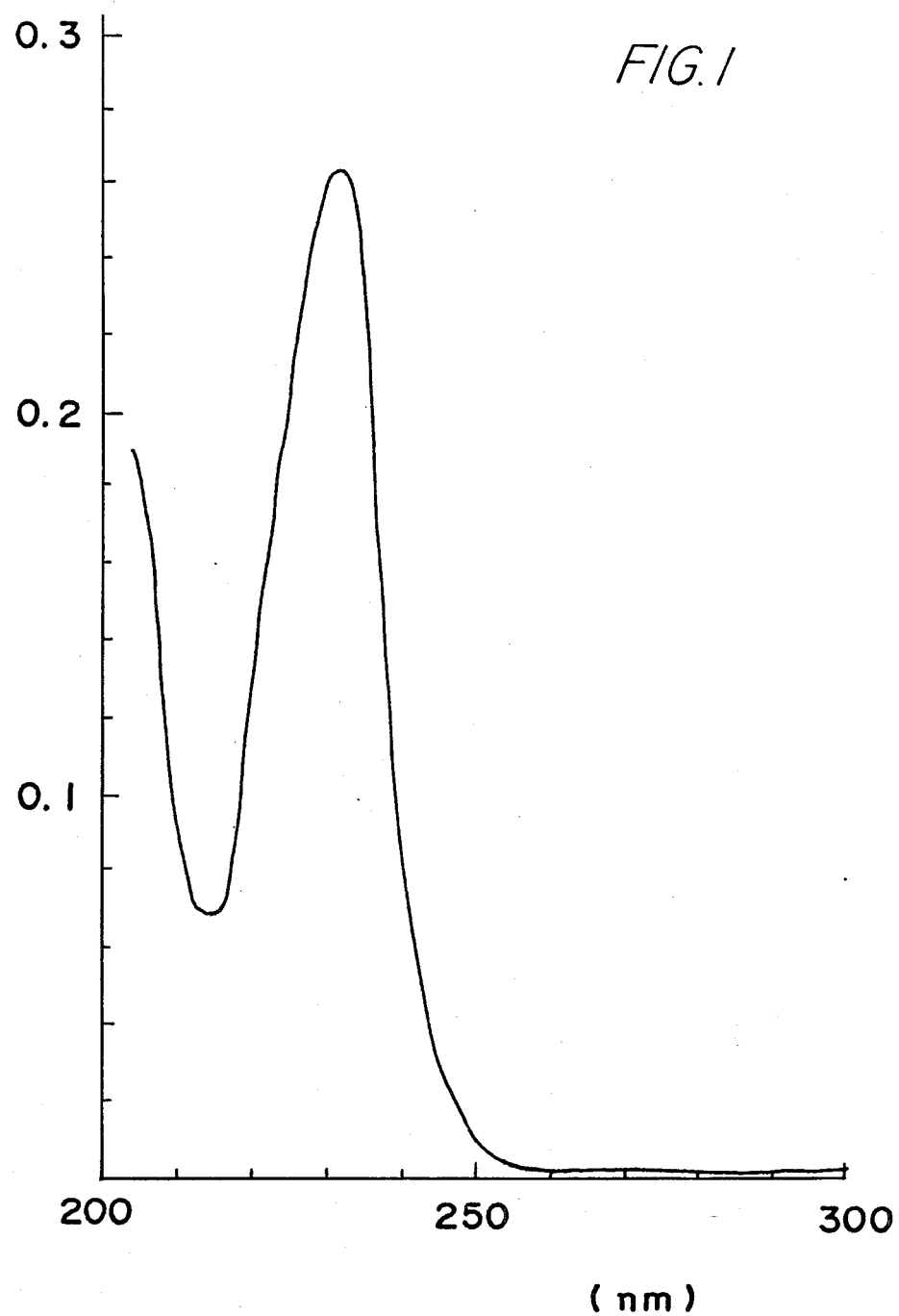
FIG. 1 shows the UV absorption spectrum of PTL-448-A (in methanol)
Figure 2:
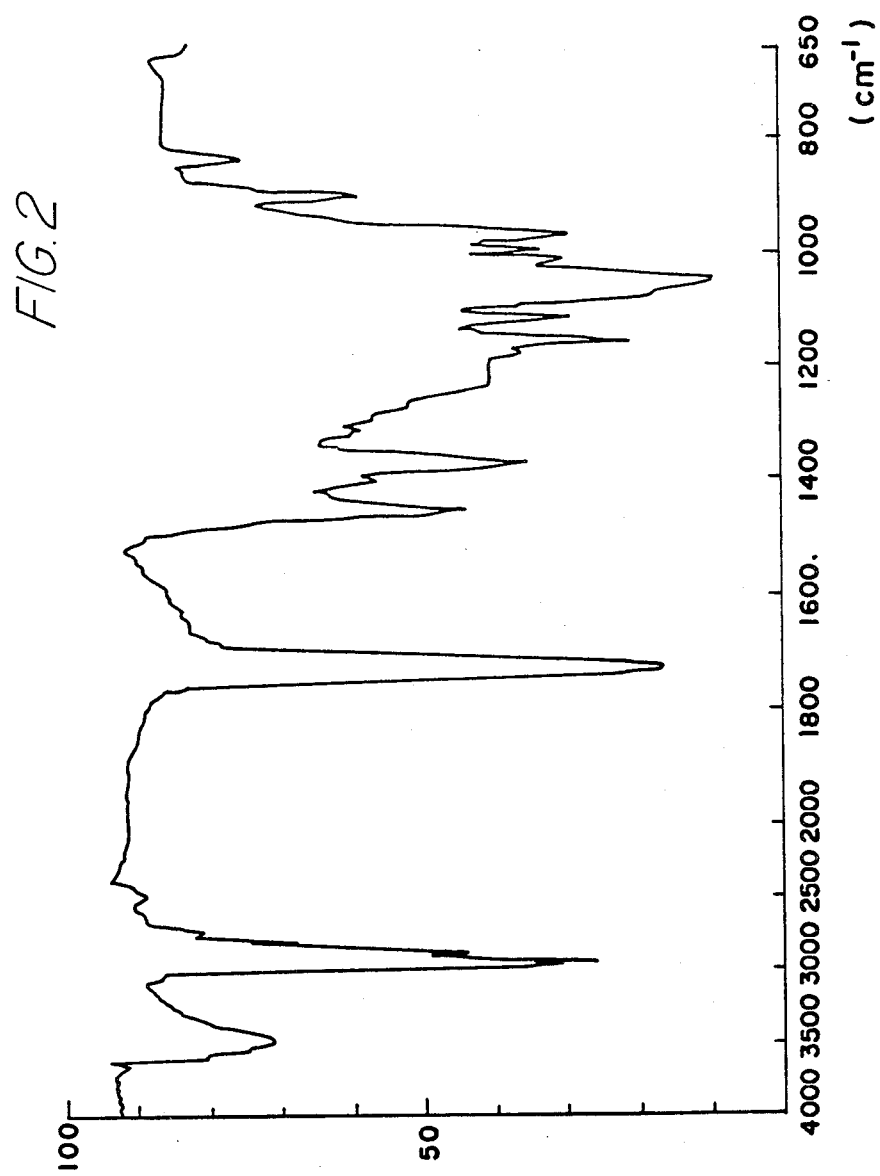
FIG. 2 the IR absorption spectrum of PTL-448-A (KBr)
Figure 3:
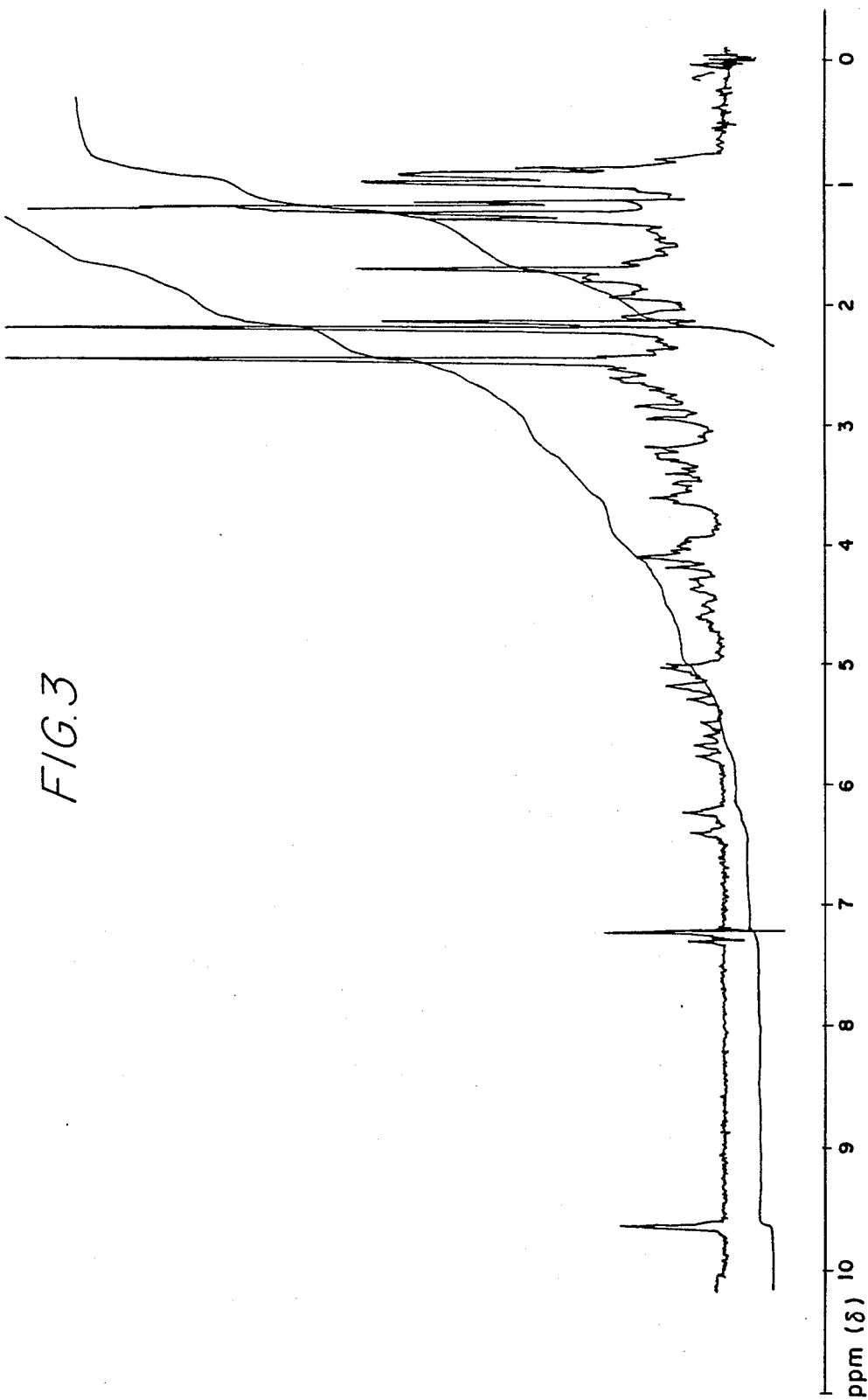
FIG. 3 the proton NMR spectrum of PTL-448-A (in $CDCl_3$)
Figure 4:
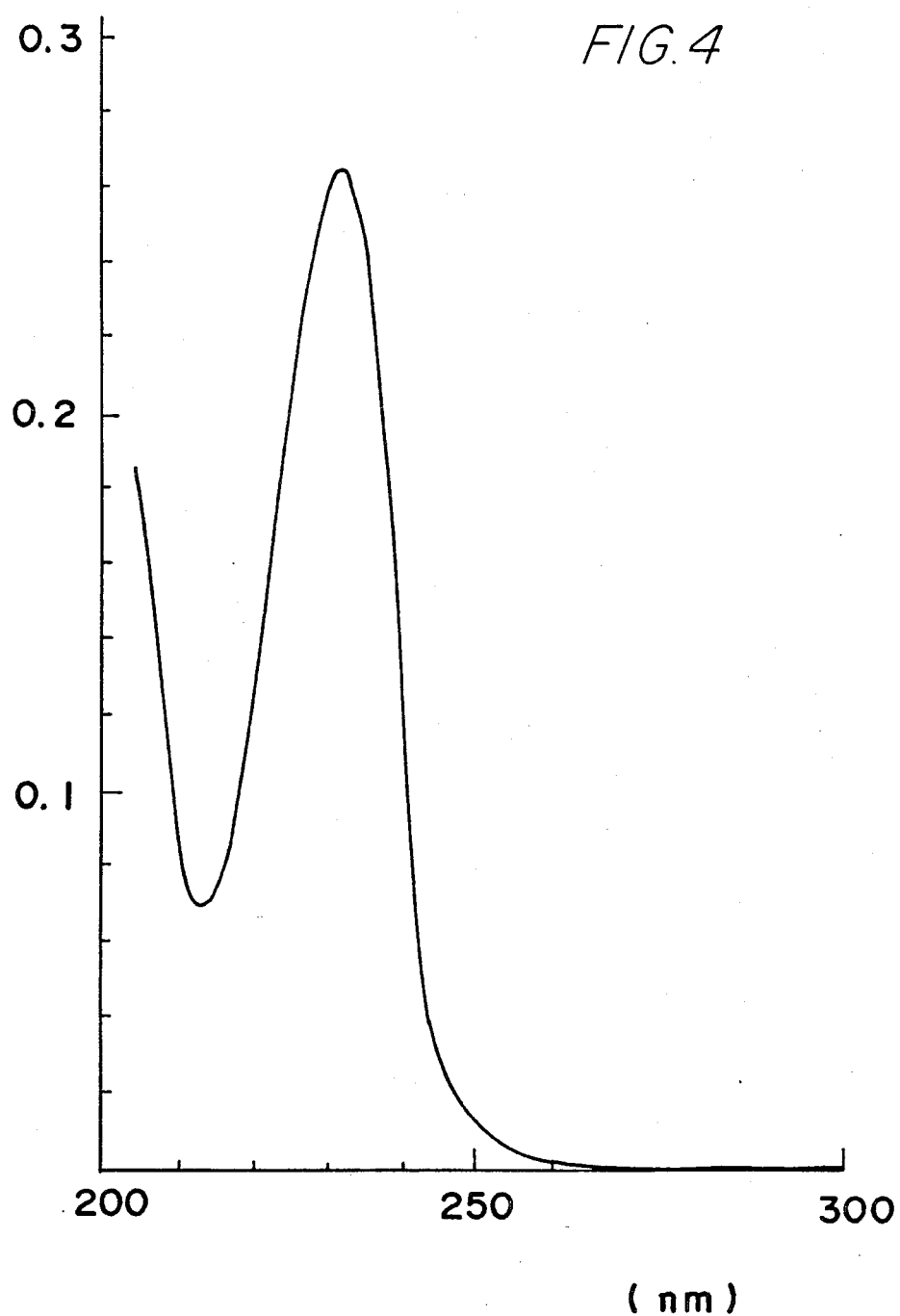
FIG. 4 the UV absorption spectrum of PTL-448-B (in methanol)
Figure 5:
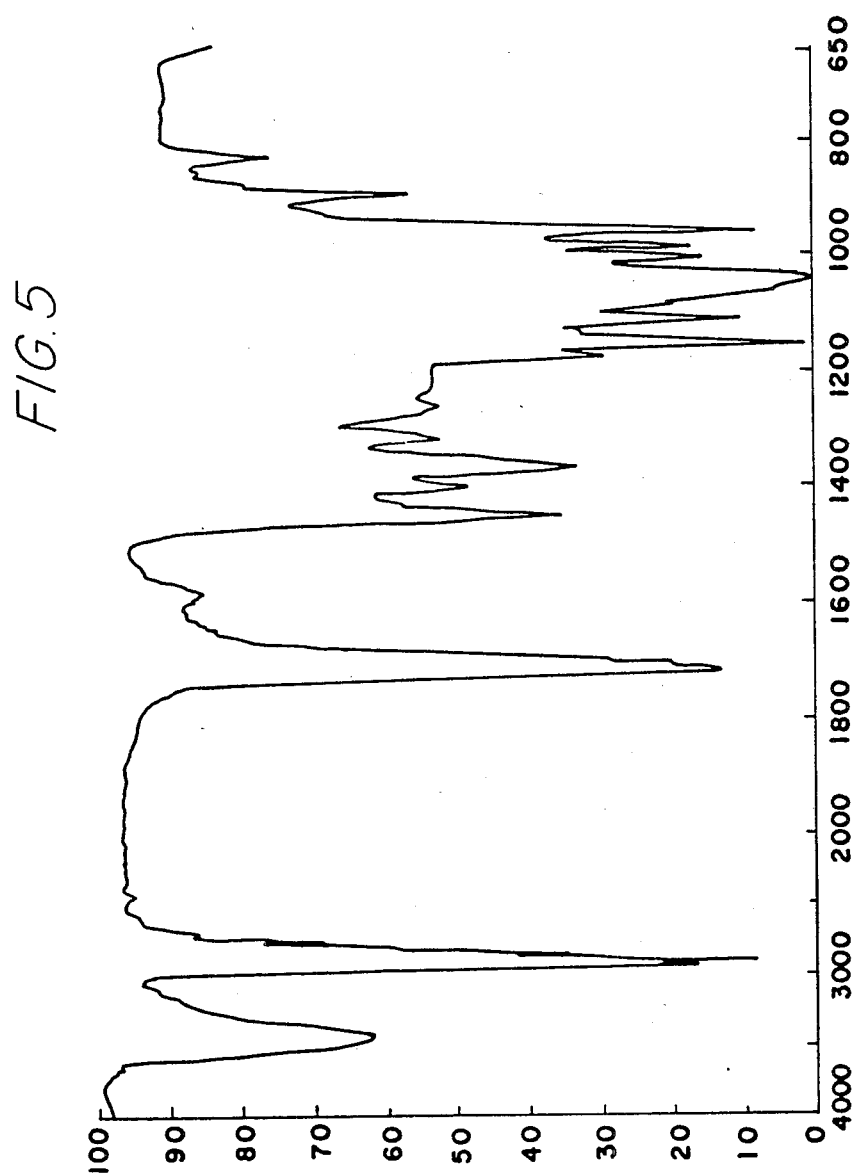
FIG. 5 the IR absorption spectrum of PTL-448-B (KBr)
Figure 6:
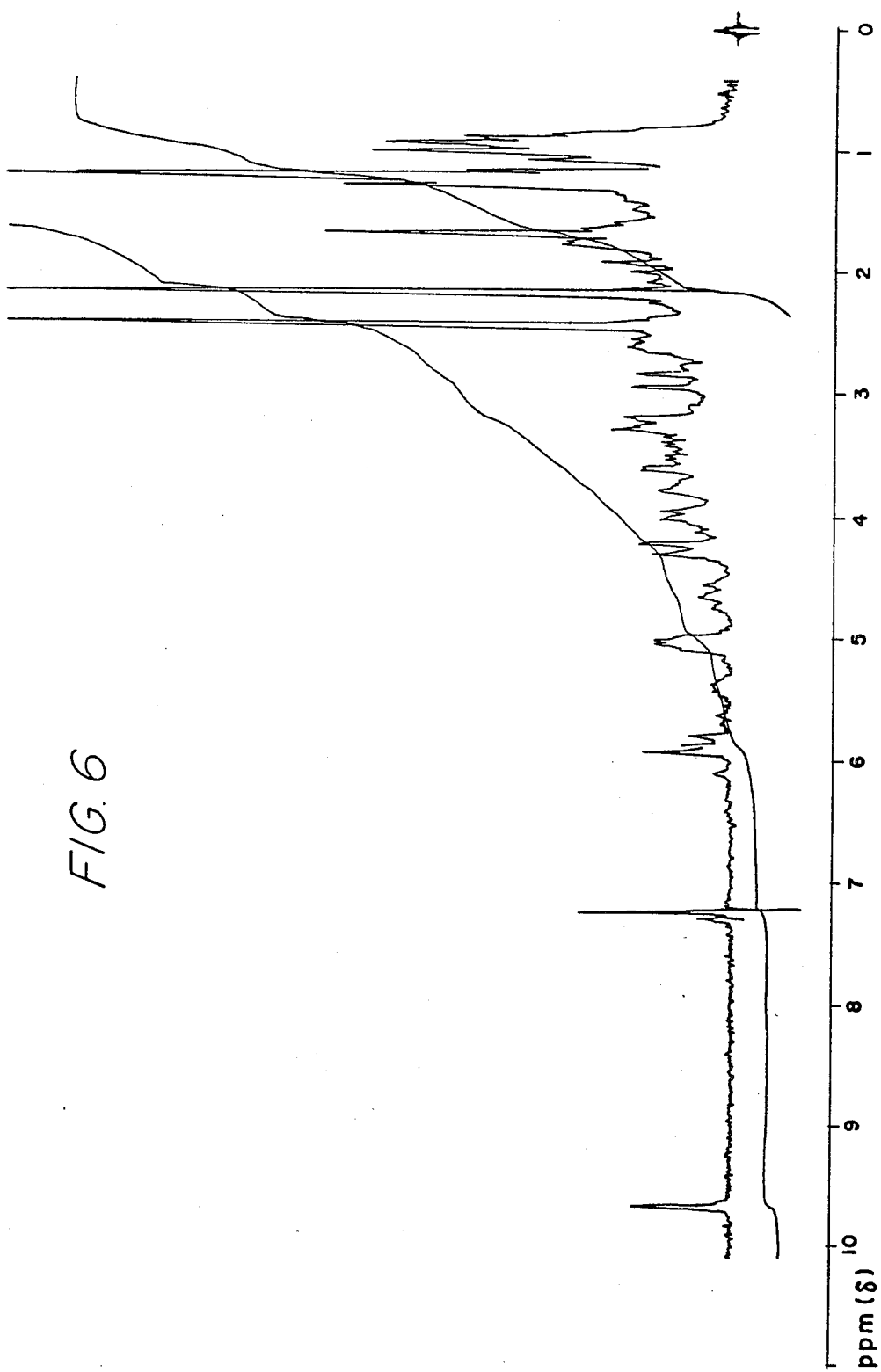
FIG. 6 the proton NMR spectrum of PTL-448-B (in $CDCl_3$)
Figure 7:
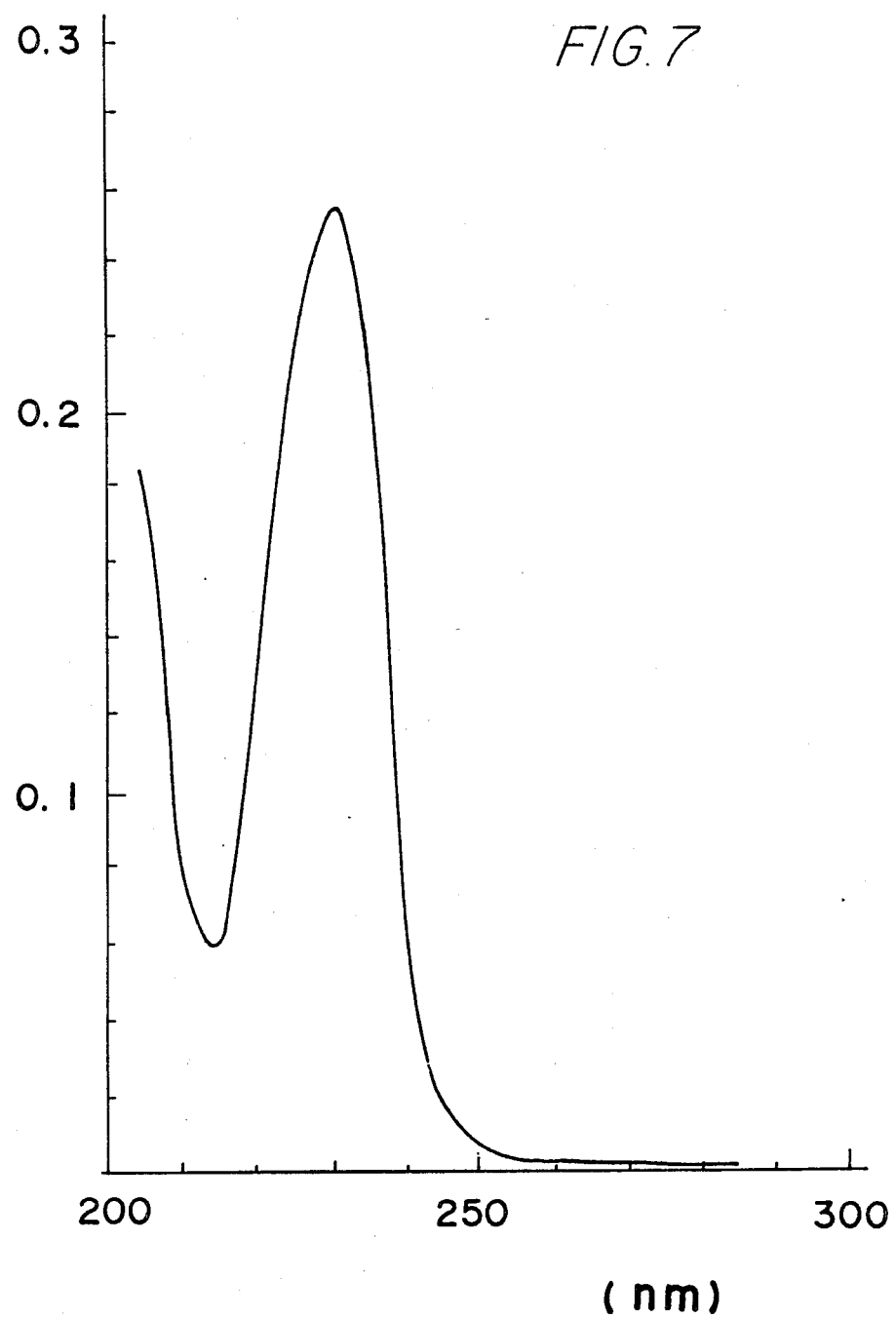
FIG. 7 the UV absorption spectrum of PTL-448-C (in methanol)
Figure 8:
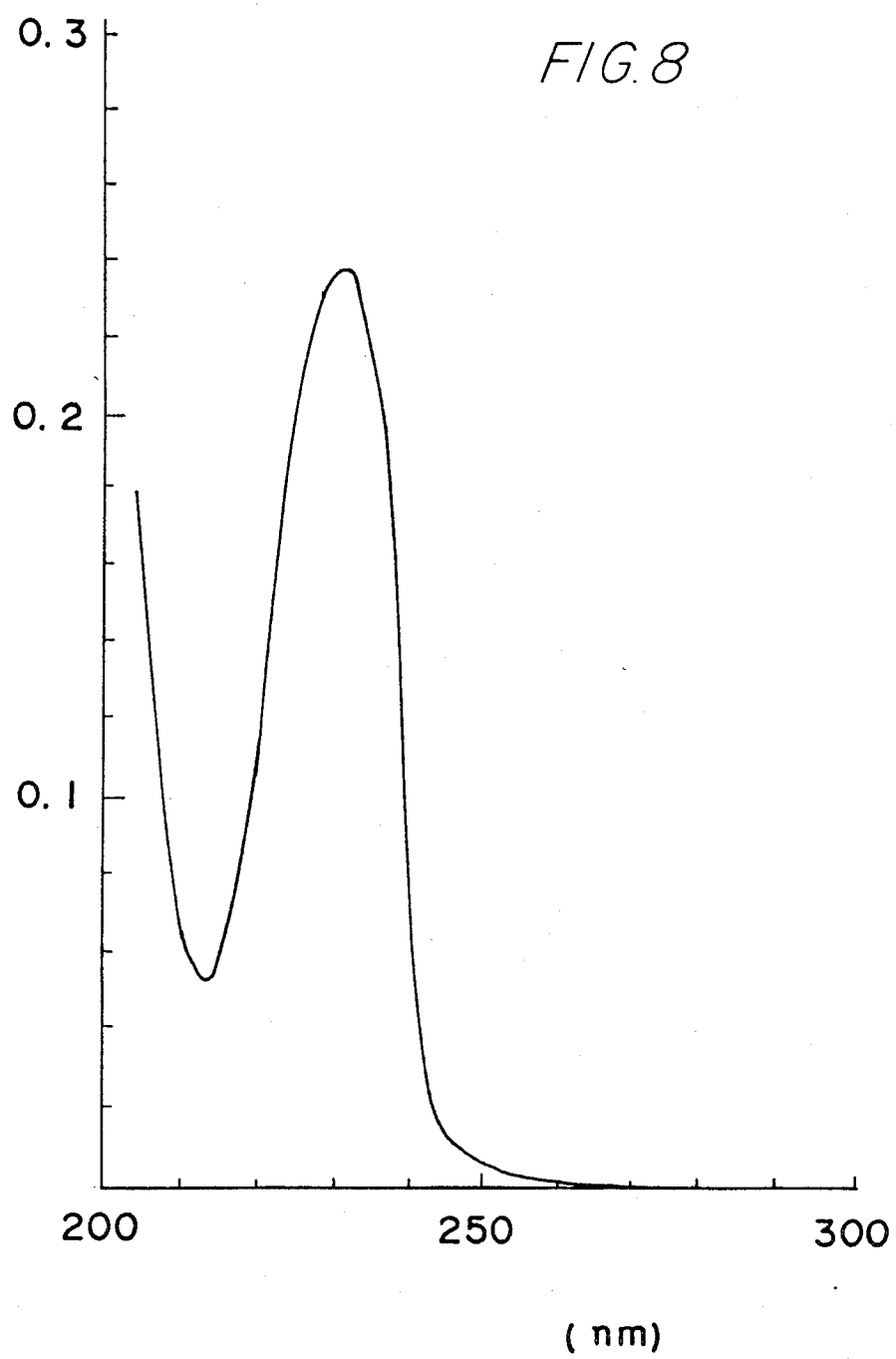
FIG. 8 shows the UV absorption spectrum of PTL-448-D (in methanol).

| | | PTL-448-A | PTL-448-B | PTL-448-C | PTL-448-D |
|---|---|---|---|---|---|
| (a) | Elemental analysis: | | | | |
| | C (%): | 63.73 | 62.45 | 64.78 | 63.82 |
| | H (%): | 9.85 | 9.18 | 9.24 | 9.26 |
| | N (%): | 2.92 | 3.25 | 3.57 | 3.97 |
| (b) | Melting point (°C.): | 108–110 | 114–115 | 91–93 | 98–100 |
| (c) | Molecular formula: | $C_{48}H_{82}N_2O_{14}$ | $C_{46}H_{80}N_2O_{13}$ | $C_{41}H_{70}N_2O_{11}$ | $C_{39}H_{68}N_2O_{10}$ |
| (d) | Molecular weight: | 910 | 868 | 766 | 724 |
| (e) | Optical rotation $[\alpha]_D^{22}$: | (c = 1, $CHCl_3$) +40.0° | (c = 1, $CHCl_3$) +14.4° | (c = 0.5, $CHCl_3$) −15.9° | (c = 0.5, $CHCl_3$) +23.2° |
| (f) | UV spectrum (in MeOH): | FIG. 1 | FIG. 4 | FIG. 7 | FIG. 8 |
| (g) | IR spectrum (KBr method): | FIG. 2 | FIG. 5 | — | — |
| (h) | $^1H$-NMR spectrum (in $CDCl_3$): | FIG. 3 | FIG. 6 | — | — |
| (i) | $^{13}C$-NMR spectrum (in $CDCl_3$): | Table 2(A) | Table 2(B) | — | — |
| | (The properties below are common to all of PTL-448-A, B, C and D.) | | | | |
| (j) | Solubility: Soluble: methanol, ethanol, acetone, ethyl acetate, chloroform, benzene Slightly soluble: ether, n-hexane Insoluble: water | | | | |
| (k) | Color test: Positive: Dragendorff, anisaldehyde-sulfuric acid, 2,4-dinitrophenylhydrazine Negative: ninhydrin, $FeCl_3$, Reidon-Smith | | | | |
| (l) | Other property: basic compound | | | | |

TABLE 2

| (A): Chemical shift value (ppm) of $^{13}$C-NMR spectrum (in $CDCl_3$) of PTL-448-A |
|---|
| 202.3, 171.1, 170.8, 137.1, 135.9, 133.0, 128.8, 104.2, 101.1, 96.4, 80.5, 79.1, 76.4, 74.8, 73.8, 73.3, 71.7, 70.1, 69.4, 68.8, 66.1, 44.0, 42.0, 41.0, 40.7, 38.9, 37.8, 34.3, 31.3, 30.7, 25.4, 25.0, 21.4, 19.1, 19.0, 18.5, 18.3, 16.8, 15.9, 12.7, 10.0, 9.5 |

| (B): Chemical shift value (ppm) of $^{13}$C-NMR spectrum (in $CDCl_3$) of PTL-448-B |
|---|
| 202.7, 174.9, 135.1, 134.8, 133.9, 129.5, 105.0, 102.4, 96.3, 82.6, 79.4, 76.5, 74.6, 73.8, 71.4, 69.4, 69.0, 66.0, 64.8, 44.1, 42.0, 41.0, 40.7, 39.0, 38.0, 37.3, 33.2, 31.2, 30.5, 25.4, 24.8, 19.3, 19.1, 18.5, 18.3, 16.7, 16.6, 12.9, 9.6, 8.3 |

PTL-448-A, B, C and D are assumed to have the following structures:

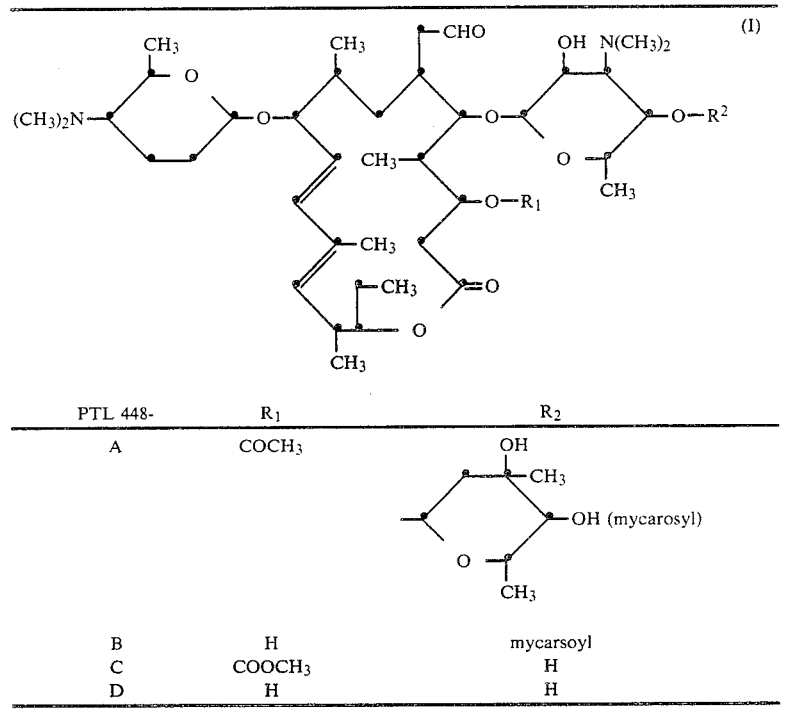

| PTL 448- | $R_1$ | $R_2$ |
|---|---|---|
| A | $COCH_3$ | OH, CH₃, OH (mycarosyl), O, CH₃ |
| B | H | mycarsoyl |
| C | $COOCH_3$ | H |
| D | H | H |

Although the stereochemistry is not shown in structure I, it is believed that the various constituent parts of the molecule have the same stereochemical configuration as possessed by protylonolide (central lactone), forosamine (left-hand sugar) and mycaminose (right-hand sugar). The stereochemical configuration of the protylonolide-forosamine linkage is believed to be 9-α-0-β-forosaminyl.

Those skilled in the art will immediately appreciate that the existence of amino functions in the structure of formula (I) means that the free bases are capable of forming acid-addition salts. Such salts, so long as they are sufficiently non-toxic to be useful in the chemotherapy of warm-blooded animals, i.e., pharmaceutically-acceptable salts, are useful as antibiotics in accordance with the invention.

Representative salts of this type include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic and cinnamic acids.

The PTL-448 macrolides can be produced by cultivating the *Streptomyces ambofaciens* strain in the presence of the macrolide intermediates described supra.

The macrolide intermediates added to the culture medium may be used singly or in combination.

They are preferably present in the culture medium at a concentration of from 10 to 500 μg/ml.

The yield of product can be increased by using an enzyme inhibitor, such as cerulenin (see *Methods in Enzymology*, 72, 520 (1981)). A preferred concentration range of the enzyme inhibitor, for example, cerulenin in the culture medium is 10 to 200 μg/ml.

Suitable culture media in accordance with the present invention include any of the conventional synthetic and natural media in liquid or solid form so long as the strain used grows therein and the PTL-448 substance is formed from protylonolide and the related compounds. Suitable media are those commonly used for the production of antibiotics by fermentation of *Actinomycetes* such as *Streptomyces*. As examples of carbon sources there may be mentioned glucose, maltose, sucrose, starch, dextrin, glycerin, animal oils and vegetable oils. As nitrogen sources, there may be mentioned various nitrogen-containing substances such as yeast extracts, meat extracts, peptone, soybean powder, dry yeast, ammonia, and urea. In addition to these, a source of inorganic salts such as phosphates and salts of metals such as magnesium, potassium, sodium, iron, manganese, cobalt, etc. may be used if the need arises.

The microorganism should be cultured under aerobic conditions, such as by using a shaking culture, aeration-agitation culture, etc. The culture temperature is generally from 20° to 40° C.

The yield of the PTL-448 derivative can also be increased by separately preparing the sugar moieties contained in the PTL-448 molecule and adding them to the culture medium. These kind of sugars can be obtained by the chemical decomposition of spiramycin and tylosin. The culture period is generally 1 to 10 days, and during this period, the PTL-448 derivatives are formed and accumulate inside and outside the mycelium. After completion of cultivation, the PTL-448 derivative can be separated from the culture medium using those conventional techniques commonly used in connection with basic lipid-soluble substances. For example, the mycelium can be separated from the filtrate, and the PTL-448 derivative extracted from the filtrate with an organic solvent such as ethyl acetate, benzene or the like and then concentrated. The PTL-448 derivative can be similarly extracted from the mycelium with aqueous acetone, aqueous methanol or the like and then concentrated.

Thereafter, the PTL-448 derivative can be purified by well-known purification methods such as column chromatography with silica gel or alumina, thin layer chromatography and the like.

The direct products of the fermentation, i.e., PTL-448A and B, can be converted to their demycarosyl analogues, i.e., PTL-448C and PTL-448D, by acid hydrolysis. For example, PTL-448-C and D can be produced by dissolving either one or both PTL-448-A and B in an organic solvent, and stirring at acid pH to form the PTL-448 derivatives C and D which can then be recovered from the reaction mixture. Of course, the PTL-448 C and D derivatives can also be formed directly during the cultivation by variation of the fermentation conditions. Thus, if a microorganism is used which lacks the mycarose biosynthetic ability, or an ability to bind mycarose to macrolide-type aglycones, direct formation of the PTL-448 C and D derivatives will occur. The acid used to effect the acid hydrolysis may be a strong mineral acid such as hydrochloric acid or sulfuric acid or an organic acid such as formic acid. The pH during the hydrolysis should preferably be in the range of from 1 to 3.

The hydrolysis can be effected in the culture medium itself or on the PTL-448 A and B derivatives isolated from the culture medium. In either case a suitable temperature for effecting the hydrolysis will lie in the range from 10 to 80° C. The period of time needed to accomplish the hydrolysis will normally vary from 10 minutes to 10 hours but account should be taken of the stability of the PTL-448 derivatives.

To further illustrate the invention reference will now be made to the following non-limiting Examples.

EXAMPLE 1

*Streptomyces ambofaciens* ATCC 15154 (NRRL 2420) was used as the seed microorganism. Said strain was placed in 100 ml of a seed culture medium (glucose, 2.0%; meat extract, 0.5%; peptone, 0.5%; dry yeast, 0.3%; sodium chloride, 0.5%; $CaCO_3$, 0.3%; and pH, 7.0) in a 500 ml Sakaguchi's flask, and the culture was shaken at 27° C. for 48 hours. The seed culture medium thus obtained was transferred to 100 ml of a fermentation medium (glucose, 1.0%; dry yeast, 1.0%; sodium chloride, 0.5%; $CaCO_3$, 1.0%; $NaNO_3$, 0.1%; and pH, 7.5) in a 500 ml Sakaguchi's flask at a rate of 1% by volume based on the medium, followed by culture at 27° C. At the beginning of the culture and 24 and 48 hours thereafter, cerulenin, in solution in a little ethanol, was added to the flask, at a rate of 4 mg per flask. Further, 24 hours after the beginning of the culture, protylonolide, in solution in a little ethanol, was added to the flask at a rate of 10 mg per flask. The culture was continued for 72 hours during which the pH of the medium was not controlled.

The mycelium and precipitate were filtered off from the culture media of 100 Sakaguchi's flasks to obtain 8.5 liters of a filtrate. The filtrate was adjusted to a pH of 8.5 with a 6N sodium hydroxide solution and extracted twice with the same amount of benzene. The benzene layer was concentrated to dryness to obtain 1.3 g of a yellow powder. This powdery sample, after being suspended in chloroform, was added to a column packed with silica gel (Art. 7734 produced by Merck) and eluted with chloroform/methanol/conc. aqueous ammonia (10/1/0.05). Each fraction (20 ml) was analysed by thin layer chromatography on silica gel (Art. 5554 Merck, developing solvent, chloroform/methanol/-conc. aqueous ammonia (15/1/0.05)) to locate those fractions containing a compound having an Rf value of about 0.26. These fractions were collected and concentrated under reduced pressure to obtain 96 mg of a mixture of PTL-448-A and PTL-448-B as a white powder.

To further separate these substances thin layer chromatography on alumina (Art. 5550 Merck, developing solvent, ethyl acetate/benzene (6/1)) was carried out. The bands at Rf values of 0.6 and 0.4 were collected, eluted with ethyl acetate and concentrated to obtain 37 mg of PTL-448-A and 45 mg of PTL-448-B, respectively, as white powders. The physico-chemical properties of the PTL-448 substances were as shown in Table 1 and Tables 2(A) and 2(B).

EXAMPLES 2-4

Example 1 was repeated except that protylonolide, a substance to be added as starting material one day after the beginning of culture, was replaced by 5-O-mycaminosylprotylonolide, 20-hydroxy-5-O-mycaminosylprotylonolide or 20-oxo-5-O-mycaminosyl-protylonolide, and that each substance was added at a rate of 15 mg per flask. Three days after the initiation of culture, PTL-448-A and B were formed and accumulated in the culture medium, in the amounts shown in Table 5. The yields were determined by extracting the culture medium with benzene, concentrating the extract, dissolving the residue in methanol, and then according to Example 1, separating and purifying the residue by thin layer chromatography on alumina/silica gel and scanning (UV) at 232 nm.

TABLE 5

| | | Output of PTL-448 ($\mu$g/ml) | |
|---|---|---|---|
| Example | Starting Material | A | B |
| 2 | 5-O—Mycaminosyl-protylonolide | 10 | 11 |
| 3 | 20-Hydroxy-5-O—mycaminosyl-protylonolide | 5 | 8 |
| 4 | 20-Oxo-5-O—mycaminosyl-protylonolide | 19 | 20 |

EXAMPLE 5

Example 1 was repeated except that *Streptomyces ambofaciens* E. B. Shirling ISP 5219 (ATCC 23877) was used as the seed microorganism. As a result, it was found that 1.2 μg/ml of PTL-448-A and 3.5 μg/ml of PTL-448-B were formed and accumulated in the culture medium. The seed microorganism of Example 1 formed 15 μg/ml of PTL-448-A and 21 μg/ml of PTL-448-B in a similar experiment.

EXAMPLE 6

One hundred milligrams of PTL-448-A were dissolved in 5 ml of methanol acidified with hydrochloric acid (pH 2) and stirred at 42° C. for 2 hours. The pH of the reaction solution was raised to 9 with sodium hydroxide, and the solution then extracted with benzene. The residue was dissolved in a little methanol and subjected to thin layer chromatography (silica gel, developed with chloroform/methanol/conc. aqueous ammonia (10/1/0.05)). The product at an Rf value of about 0.4 was collected and concentrated to obtain 45 mg of PTL-448-C as a white powder. The physico-chemical properties of this substance were as shown in Table 1.

EXAMPLE 7

Five milliliters of a 0.1N hydrochloric acid/methanol (1/3) solution containing 20 mg of PTL-448-A were stirred overnight at room temperature. The reaction mixture was worked up, using the procedure of Example 6, to obtain 8.4 mg of PTL-448-C.

EXAMPLE 8

The procedure of Example 6 was repeated except that 100 mg of PTL-448-B was dissolved in 5 ml of methanol acidified with hydrochloric acid to pH 2. Thus, 41 mg of PTL-448-D were obtained as a white powder. The physico-chemical properties of this substance were as shown in Table 1.

The antimicrobial activity of the PTL-448 derivatives of the invention is illustrated in Table 3, which is a summary of the results of a number of tests carried out to determine minimum inhibitory concentrations (MIC) of the derivatives against a number of typical bacteria. Comparative results for Spiramycin I (SPM I) and III (SPM III) are also given. Tests were carried out using heart infusion agar media (pH 7 at 37° C., after about 20 hours).

TABLE 3

| Antimicrobial Activity of PTL-448 Derivatives | | | | | | |
|---|---|---|---|---|---|---|
| | MIC (μg/ml) | | | | | |
| Test Organism | A | B | C | D | SPM I | SPM III |
| *Staphylococcus aureus* ATCC 6538P | 6.25 | 3.12 | 1.56 | 1.56 | 6.25 | 12.5 |
| *S. aureus* FDA 209P | 6.25 | 3.12 | 1.56 | 1.56 | 6.25 | 12.5 |
| *Bacillus subtilis* PCI 219 | 1.56 | 0.78 | 1.56 | 1.56 | 1.56 | |
| *B. cereus* IFO 3001 | 3.12 | 1.56 | 1.56 | 1.56 | 3.12 | 3.12 |
| *Micrococcus luteus* ATCC 9341 | 0.4 | 0.4 | 0.4 | 0.2 | 0.4 | 0.4 |
| *Streptococcus pneumoniae* III KB 165 | 0.4 | 0.4 | 0.2 | 0.2 | 0.4 | 0.4 |
| *S. pyogenes* KB 166 | N.D. | 0.4 | 0.4 | 0.4 | N.D. | N.D. |
| *E. coli* N-33 | 1.56 | 0.78 | 0.4 | 0.2 | 1.56 | 1.56 |

TABLE 3-continued

| Antimicrobial Activity of PTL-448 Derivatives | | | | | | |
|---|---|---|---|---|---|---|
| | MIC (μg/ml) | | | | | |
| Test Organism | A | B | C | D | SPM I | SPM III |
| *Klebsiella pneumoniae* ATCC 10031 | >100 | >100 | 50 | 25 | >100 | >100 |
| *Salmonella typhimurium* KB 20 | >100 | >100 | 50 | 25 | >100 | >100 |

N.D.: Not determined.

In addition, the activity of the PTL-448 derivatives against *Mycoplasma* was examined by conventional methods (paper disk 8 mm in diameter, 37° C., about 48 hours). The results of these tests are shown in Table 4:

TABLE 4

| | Diameter of Inhibition Zone (mm) | | | |
|---|---|---|---|---|
| Test Microorganism | PTL-448-A | -B | -C | -D |
| *Mycoplasma gallisepticum* KP-13 | 29.2 | 30.1 | — | — |
| *Acholeplasma laidlawii* PG-8 | 32.6 | 31.4 | 33.1 | 32.0 |

Thus, the compounds of the invention are useful in the treatment or control of bacterial or *Mycoplasma* infections in warm-blooded animals, including humans.

For this purpose the novel active ingredients of the invention will normally be formulated with those excipients and carriers common in the pharmaceutical and animal health arts. Such carriers and excipients may be similar to those used in connection with spiramycin or tylosin. Dosage regimes may be similar to those used in connection with the aforementioned antibiotics.

In one aspect of the invention there is provided a pharmaceutical or veterinary formulation comprising as an active ingredient a novel compound of thereof, associated with one or more physiologicallyacceptable carriers therefor.

The low toxicity of the PTL-448 derivatives of the invention has been illustrated by tests in mice where no fatalities occurred after 1 month of treatment with the compounds (A, B, C and D, 100 mg/kg i.p.).

I claim:

1. PTL-448-A, which has the following physico-chemical properties:

(a) Elemental analysis (approximate values)
   C(%) 63.73
   H(%): 9.85
   N(%): 2.92

(b) Melting point: 108°–110° C.

(c) Molecular formula: $C_{48}H_{82}N_2O_{14}$ (d) Molecular weight: 910

(e) Optical rotation $[\alpha]_D^{22} +40.0°$ (c=1, CHCl$_3$)

(f) $^{13}$C-NMR spectrum (in CDCl$_3$) Chemical shift values (ppm): 202.3, 171.1, 170.8, 137.1, 135.9, 133.0, 128.8, 104.2, 101.1, 96.4, 80.5, 79.1, 76.4, 74.8, 73.8, 73.3, 71.7, 70.1, 69.4, 68.8, 66.1, 44.0, 42.0, 41.0, 40.7, 38.9, 37.8, 34.3, 31.3, 30.7, 25.4, 25.0, 21.4, 19.1, 19.0, 18.5, 18.3, 16.8, 15.9, 12.7, 10.0, 9.5 and its acid-additions salts.

2. PTL-448-B, which has the following physicochemical properties:

(a) Elemental analysis (approximate values)
   C(%): 62.45
   H(%): 9.18

N(%): 3.25
(b) Melting point: 114°–115° C.
(c) Molecular formula: $C_{46}H_{80}N_2O_{13}$
(d) Molecular weight: 868
(e) Optical rotation: $[\alpha]_D^{22} +14.4°$ (c=1, CHCl$_3$)
(f) $^{13}$C-NMR spectrum (in CDCl$_3$) Chemical shift values (ppm): 202.7, 174.9, 135.1, 134.8, 133.9, 129.5, 105.0, 102.4, 96.3, 82.6, 79.4, 76.5, 74.6, 73.8, 71.4, 69.4, 69.0, 66.0, 64.8, 44.1, 42.0, 41.0, 40.7, 39.0, 38.0, 37.3, 33.2, 31.2, 30.5, 25.4, 24.8, 19.3, 19.1, 18.5, 18.3, 16.7, 16.6, 12.9, 9.6, 8.3
and its acid addition salts.

3. PTL-448-C having the following physicochemical properties:
(a) Elemental analysis (approximate values
C(%): 64.78
H(%): 9.24
N(%): 3.57
(b) Melting point: 91°–93° C.
(c) Molecular formula: $C_{41}H_{70}N_2O_{11}$
(d) Molecular weight: 766
(e) Optical rotation $[\alpha]_D^{22}$: $-15.9°$ (c=0.5, CHCl$_3$)
and its acid addition salts.

4. PTL-448-D having the following physicochemical properties:
(a) Elemental analysis (approximate values)
C(%): 63.82
H(%): 9.26
N(%): 3.97
(b) Melting point: 98°–100° C.
(c) Molecular formula: $C_{39}H_{68}N_2O_{10}$
(d) Molecular weight: 724
(e) Optical rotation $[\alpha]_D^{22} +23.2°$ (c=0.5, CHCl$_3$)
and its acid addition salts.

5. A macrolide of formula (I):

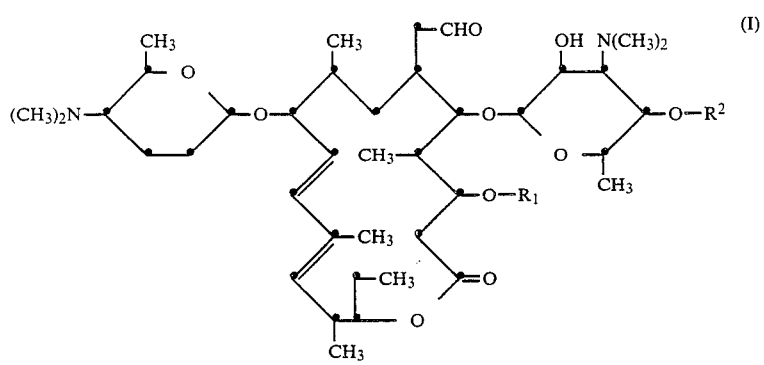

wherein $R^1$ is hydrogen or acetyl, and $R^2$ is hydrogen or mycarosyl; or a pharmaceutically-acceptable salt thereof.

6. A macrolide of claim 5 in the form of the free base.

7. The macrolide of claim 5 wherein $R^1$ and $R^2$ are hydrogen.

8. The macrolide of claim 5 wherein $R^1$ is acetyl and $R^2$ is hydrogen.

9. A method for treating susceptible bacterial or Mycoplasma infections in warm-blooded animals which comprises administering to the animal an effective amount of PTL-448 derivative A as described in claim 1 or a pharmaceutically-acceptable salt thereof.

10. A method for treating susceptible bacterial or Mycoplasma infections in warm-blooded animals which comprises administering to the animal an effective amount of PTL-448 derivative B as described in claim 2 or a pharmaceutically-acceptable salt thereof.

11. A method for treating susceptible bacterial or Mycoplasma infections in warm-blooded animals which comprises administering to the animal an effective amount of PTL-448 derivative C as described in claim 3 or a pharmaceutically-acceptable salt thereof.

12. A method for treating susceptible bacterial or Mycoplasma infections in warm-blooded animals which comprises administering to the animal an effective amount of PTL-448 derivative D as described in claim 4 or a pharmaceutically-acceptable salt thereof.

13. A pharmaceutical or veterinary formulation comprising as an active ingredient PTL-448 derivative A as described in claim 1, or a pharmaceuticallyacceptable salt thereof, associated with one or more physiologically-acceptable carriers.

14. A pharmaceutical or veterinary formulation comprising as an active ingredient PTL-448 derivative B as described in claim 2, or a pharmaceutically-acceptable salt thereof, associated with one or more physiologically-acceptable carriers.

15. A pharmaceutical or veterinary formulation comprising as an active ingredient PTL-448 derivative C as described in claim 3, or a pharmaceutically-acceptable salt thereof, associated with one or more physiologically-acceptable carriers.

16. A pharmaceutical or veterinary formulation comprising as an active ingredient PTL-448 derivative D as described in claim 4, or a pharmaceutically-acceptable salt thereof, associated with one or more physiologically-acceptable carriers.

* * * * *